US006451980B1

(12) United States Patent
Khaw et al.

(10) Patent No.: US 6,451,980 B1
(45) Date of Patent: Sep. 17, 2002

(54) SIGNAL ENHANCEMENT OF BISPECIFIC ANTIBODY-POLYMER PROBE FOR IMMUNOASSAY USE

(75) Inventors: Ban-an Khaw, Milton, MA (US); Jagat Narula, Brookline, MA (US)

(73) Assignee: Ban-An Khaw, Milton, MA (US)

( * ) Notice: Subject to any disclaimer, the term of this patent is extended or adjusted under 35 U.S.C. 154(b) by 0 days.

(21) Appl. No.: 09/380,168

(22) PCT Filed: Feb. 25, 1998

(86) PCT No.: PCT/US98/03638

§ 371 (c)(1),
(2), (4) Date: Oct. 6, 1999

(87) PCT Pub. No.: WO98/38513

PCT Pub. Date: Sep. 3, 1998

Related U.S. Application Data

(60) Provisional application No. 60/039,111, filed on Feb. 26, 1997.

(51) Int. Cl.[7] ............................ C07K 16/46; C07K 16/28

(52) U.S. Cl. .................... 530/387.3; 530/300; 530/350; 530/395; 530/388.8; 530/391.1; 530/391.3; 530/391.5; 530/391.7; 530/391.9; 514/2; 514/12; 514/387; 435/69.6; 435/188.5; 435/287.1; 435/289.1; 435/817; 435/518; 435/7.1; 435/317.1; 435/524; 435/525; 435/6; 435/912; 435/5; 435/7.9; 435/176; 435/7.93; 435/7.94; 435/288; 435/291; 424/1.49; 424/1.41; 424/1.45; 424/1.69; 424/9; 424/164.1; 424/85.91; 424/78.08; 424/86; 424/9.34; 424/9.35; 424/87; 424/9.36; 424/9.4; 424/9.6; 424/133.1; 424/155.1; 424/153; 424/159.1; 424/178.1

(58) Field of Search .................... 424/1.49, 1.41, 424/1.45, 1.69, 9, 164.1, 85.91, 78.08, 86, 9.34, 9.35, 87, 9.36, 9.4, 9.6, 133.1, 155.1, 1.53, 159.1, 178.1; 435/96.6, 188.5, 287.1, 289.1, 817, 518, 7.1, 317.1, 524, 525, 6, 91.2, 5, 7.9, 176, 7.93, 7.94, 288, 291; 514/2, 12, 387; 530/387.3, 395, 388.8, 391.1, 391.3, 391.5, 391.7, 391.9

(56) References Cited

U.S. PATENT DOCUMENTS 5,223,242 A    6/1993    Khaw et al. ................. 424/1.1

(List continued on next page.)

FOREIGN PATENT DOCUMENTS

| WO | WO 90/15993 | * 12/1990 | .......... G01N/33/53 |
| WO | WO 94/12196 | *  6/1994 | .......... A61K/35/00 |

OTHER PUBLICATIONS

Torchilin, V.p., et al. The antibody linked chelating polymers for nuclear therapy and diagnostics. Crit. rev. Therap. drug Carrire Syst. 1991., vol. 7, No. 4, pp. 275–308. Abstract Only.*

(List continued on next page.)

Primary Examiner—Christopher L. Chin
Assistant Examiner—Lisa V Daniels-Cook
(74) Attorney, Agent, or Firm—Pennie & Edmonds LLP

(57) ABSTRACT

An immunoassay method including reacting a sample from a patient with a bispecific antibody, wherein the bispecific antibody includes one antibody specific for a compound to be detected and a second antibody specific for a compound foreign to said patient sample, and subsequently reacting the patient sample with a polymer probe, wherein the polymer probe includes a compound recognized by the second antibody in the bispecific antibody complex and further includes at least two detectable signals; the bispecific antibody; and the polymer probe of the immunoassay method are disclosed.

6 Claims, 2 Drawing Sheets

U.S. PATENT DOCUMENTS

| | | | |
|---|---|---|---|
| 5,332,567 A | * 7/1994 | Goldenberg | 424/1.49 |
| 5,482,698 A | * 1/1996 | Griffiths | 424/141 |
| 5,591,828 A | * 1/1997 | Bosslet et al. | 530/387.3 |
| 5,698,178 A | * 12/1997 | Goldenberg | 424/1.49 |
| 5,851,527 A | * 12/1998 | Hansen | 424/178.1 |

OTHER PUBLICATIONS

Torchilin et al., "The antibody linked chelating polymers for nuclear therapy and diagnostics", Crit. Rev. Therap. Drug Carrier Syst., 7 No. 4, 275–308 (1991). These references were transmitted by the International Bureau.

Rosebrough, S.F., "Two step immunological approaches for imaging and therapy", Q.J. Nucl. Med., 40 234–251 (1996). These references were transmitted by the International Bureau.

Vuillez et al., "Two–step immunoscintigraphy for non–small cell lung cancer staging using a bispecific anti–CEA/anti––indium–DTPA antibody and an indium–111–labeled DTPA dimer", J. Nuc. Med., 38 No. 4, 507–511 (1997). These references were transmitted by the International Bureau.

Kranenborg et al., "Development and Characterization of anti–renal cell carcinoma X antichelate bispecific monoclonal antibodies for two–phase targeting of renal cell carcinoma", Canc. Res. 55, 23 Supplement 5864s–5867s (1995). These references were transmitted by the International Bureau.

Devys et al., "Comparative targeting of human colon–carcinoma multi–cell spheroids using one–and two–step (bispecific antibody) techniques", Int. J. Cancer, 67 883–891 (1996). These references were transmitted by the International Bureau.

* cited by examiner

SIGNAL ENHANCEMENT OF BISPECIFIC ANTIBODY-POLYMER PROBE FOR IMMUNOASSAY USE

CROSS REFERENCE TO RELATED APPLICATIONS

This application claims priority to U.S. Provisional Application No. 60/039,111, filed Feb. 26, 1997, and to International Application No. PCT/US98/03638, filed Feb. 25, 1998. Each of the applications cross-referenced in this section are incorporated herein by reference in its entirety.

STATEMENT REGARDING FEDERALLY SPONSORED RESEARCH OR DEVELOPMENT

BACKGROUND OF THE INVENTION

An immunoassay utilizes antibodies to detect a compound of choice. However, the sensitivity of this detection is generally limited to the amount of signal that can be carried either on an antibody, for a direct binding assay, or on the probe compound, in a competitive inhibition assay. For example, in existing immunoassays, such as radioimmunoassays, ELISA, immunofluorescent assays or immunochemiluminescent assays, too many signal entities, such as radioisotopes, horse radish peroxidase or alkaline phosphatase, attached to the detection moieties invariably inactivate the antibody or denature the antigen and change the property of he detection probe. Therefore, in order to obtain more signal, additional antibody or probe must be added. This, in turn, reduces the sensitivity of the assay, the capability of the assay to detect minute quantities of the compound in question.

For all existing immunoassays, there is lag time for the compound of interest to reach a high enough concentration in the serum to become detectable for diagnostic purposes. In the case of heart attacks, there is a delay of 4–6 hours from the onset of chest pain until the diagnostic detection of CK-MB, Troponin-T or I is possible. Myoglobin is detectable earlier, but its specificity is low. If there were an assay that could detect very minute increases of these indicator compounds in the blood at an earlier point in time, then therapeutic intervention could be started earlier and thereby bring about greater myocardial salvage. In the case of cancer detection, where, e.g., tumor associated antigens related to breast cancer or colon cancer, etc., are detected, treatment might be more effective if minute elevations of these antigens could be detected at an early stage. Therefore, there is a need to increase the sensitivity of the assay without adversely affecting the specificity of the assay system.

SUMMARY OF THE INVENTION

The invention is directed to a method to increase the sensitivity of an immunoassay, by at least 10,000 fold, without losing specificity. This improvement is achieved by the use of a bispecific antibody complex and a unique detection signal probe capable of recognizing the bispecific antibody complex.

In one aspect, the invention features an immunoassay method including reacting a sample from a patient with a bispecific antibody, wherein the bispecific antibody includes one antibody specific for a compound to be detected and a second antibody specific for a compound foreign to said patient sample, i.e., non-endogenous, and subsequently reacting the patient sample with a polymer probe, wherein the polymer probe includes a compound recognized by the second antibody in the bispecific antibody complex and further includes at least two detectable signals. The invention also features the bispecific antibody and the polymer probe of the method of the invention. Preferably, the sample from the patient is a blood or serum sample; the bispecific antibody includes an antimyosin antibody and an antibody against DTPA; and the polymer probe is a polylysine polymer and includes DTPA and at least six HRP as the detectable signal compounds.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

Figure 1A:
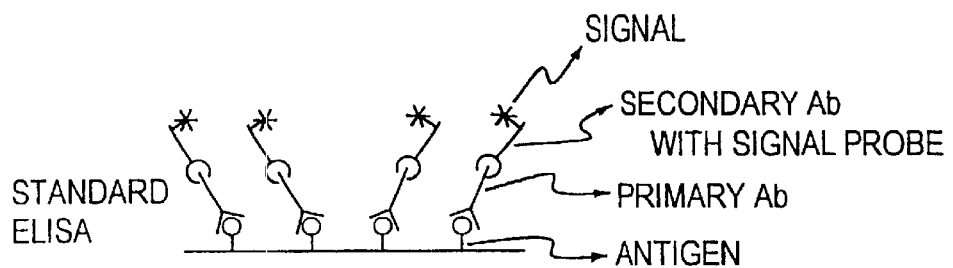
FIG. 1a shows a standard ELISA according to the prior art.
Figure 1B:
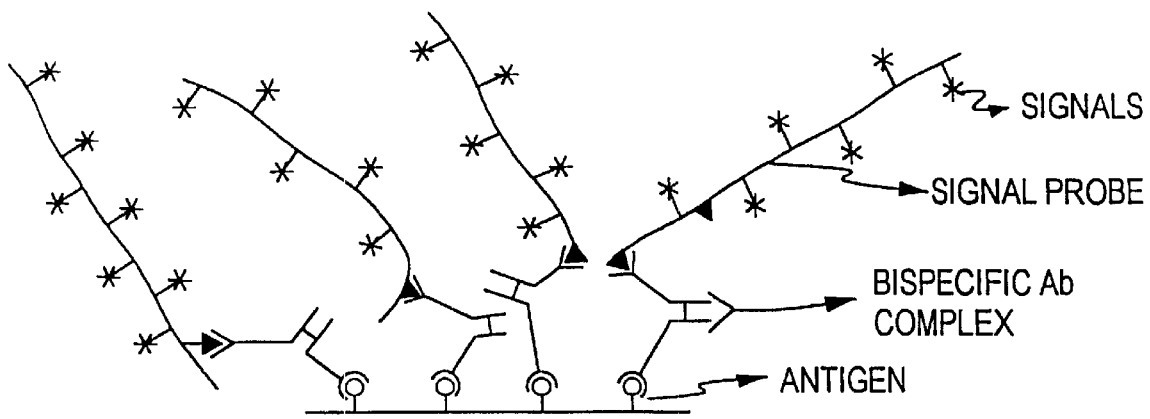
FIG. 1b shows an immunoassay according to the invention.
Figure 2:
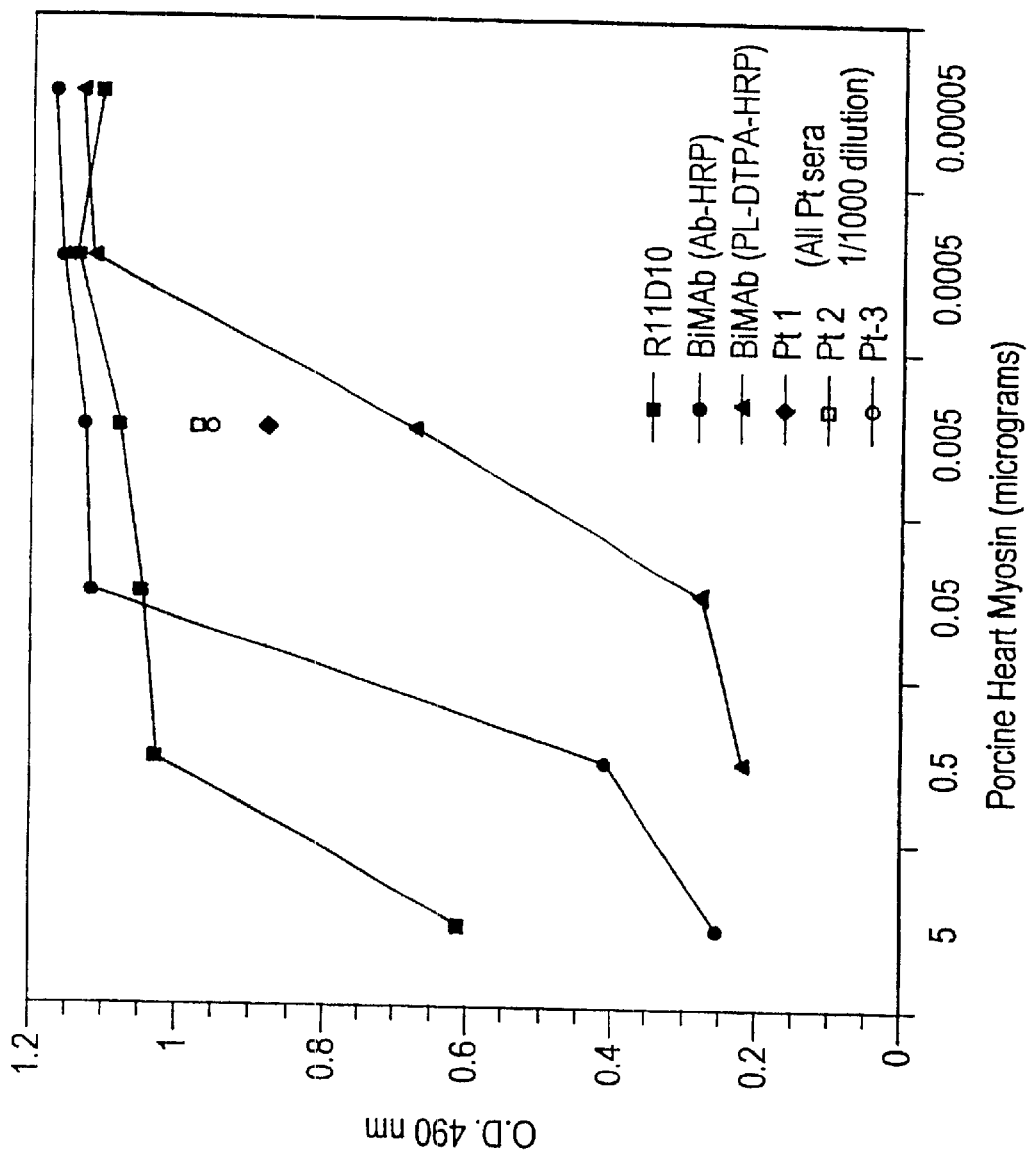
FIG. 2 is a graph showing competitive inhibition curves using standard ELISA (R11D10), bispecific antibody complex with standard secondary antibody for signal production (BiMAb (Ab-HRP)), and the method according to the invention (BiMAb(PL-DTPA-HRP)).

The invention is directed to the development of a new approach to the use of bispecific antibodies in immunoassays. The new specific antibody comprises one antibody specific for the compound associated with the pathological state to be detected and another antibody to a chemical or reporter compound that is not found naturally in man. These two are chemically or genetically linked. The bispecific antibody complex constitutes the first line of interaction with the compound one is attempting to detect. Normally many antibodies must react with the compound to enable development of sufficient signal intensity for detection. However, in the method of the invention, a novel detection probe is used, made up of any type polymer, such as polylysine or other polyamino acid, that is amenable to attachment of signal reagents and reporter compounds. The amount of signal reagent that can be used in a given assay is limited only by the size of the polymer. only a few molecules of the detection probe are therefore needed to provide this signal. The signal probe is extremely versatile as any type of signal producing compound such as radioactivity, chemical color producing enzymes or fluorescent probes can be attached to the polymer backbone. Signal amplification is not limited by the nature of the bispecific antibody complex itself.

Therefore, the immunoassay sensitivity can be amplified by at least 10,000-fold compared to conventional immunoassays or immunosandwich assays. Since early detection of many pathological states, such as acute myocardial infarction and cancer, is limited by the sensitivity of immunoassays to detect minute elevations of the pathologically associated compounds, an method and compounds of the invention will enable diagnosis of disease states at a much earlier time than previous assays, which may allow for better therapeutic intervention.

Another advantage of the method of the invention is the versatility for adaptation to any antibody. For example, the method could be adapted to detect troponin-I or T by using the antibody specific for troponin-I or T attached to a second antibody, such as the antibodies shown herein, that recognizes the detector probe. If higher sensitivity is necessary, the polymer probe could be generated to carry higher numbers of signal compounds. Furthermore, the polymer probe can include any kind of signal compound, such as radioisotope, fluorescent, or paramagnetic linked signal compounds.

All previously existing ELISA radioimmunoassays, dipstick assays for cancer, pregnancy, serum enzymes and probes and any assays utilizing antibodies could be modified according to the method of the invention to provide enhanced sensitivity. In addition, in vivo application to enhance target signal by using the method of the invention is also possible.

The following examples are presented to illustrate the advantages of the present invention and to assist one of ordinary skill in making and using the same. These examples are not intended in any way otherwise to limit the scope of the disclosure.

EXAMPLE I

Serum immunoassays for intracardiac contractile proteins constitute the mainstay for detection of myocyte necrosis associated with various cardio-vascular disorders. However, myosin heavy chain (MHC) fragments can be detected by immunoassay only after 48 h from the onset of chest pain. To enhance immunodetection of MHC, monoclonal antibody (MAb) R11D10 specific for cardiac MHC was covalently linked to MAb 4G4-1D5 specific for DTPA. The probe consisted of DTPA-modified polylysine (28:1 molar ratio) covalently linked to horse-radish peroxidase (6 moles/ mole polylysine) (PL-DTPA-HRP). Porcine cardiac myosin (PCM, 1 $\mu$/ml) was used to coat the microtiter wells. After overnight incubation and washing, three times, 50 $\mu$l each of 5 $\mu$g/ml BiMAb or MAb and serial dilutions of PCM (0.001 to 100 $\mu$g/ml) or 50$\mu$l of serial dilutions (1/1 to 1/10000) of patient sera pre-incubated for 1 h at 37° C. were added and incubated for 2 h at 37° C. After washing, the wells were incubated with goat-antimouse IgG-HRP or PL-DTPA-HRP for 2 h. A chromogen, dinitrobenzidine was used to develop the assay. The affinity of BiMAb and R11D10 were the same at 1.5×10$^9$ L/mole. The sensitivity of BiMAb was 0.5 ng, whereas that of R11D10 was 0.5 $\mu$g (1 $\mu$g/ml). BiMAb developed with the conventional goat anti-mouse IgG-HRP had a sensitivity of 0.05 $\mu$g. Therefore, BiMAb assay has a 1000 fold increase in sensitivity compared to the conventional immunoassay in the sera of 3 heart transplant patients. Using the BiMAb assay, 2.5, 1.25 and 1.3 ng MHC/50 $\mu$l serum at $\frac{1}{10^3}$ dilution, were detected. This BiMAb technology can be used in RIA or ELISA by interchanging the HRP probe for radiolabeled probe and should provide more specific in vitro diagnosis of acute myocardial infarction since detection of MHC is not feasible at the present time of day 1 of myocardial infarction by conventional immunoassays.

EXAMPLE II

In a subsequent experiment the DTPA-modified polylysine probe of Example I was covalently linked to 12 moles of horse-radish peroxidase per mole of polylysine. The results of the study show that the sensitivity of the bispecific assay of the invention ($10^{-5}$ to 100 $\mu$g/ml) was at least 10,000 fold better than the conventional immunoassay (0.1 $\mu$g/ml).

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A bispecific antibody complex comprising:
a bispecific antibody comprising a first antibody specific for a first antigen to be assayed in a sample, said first antibody being linked to a second antibody specific for a second antigen that is not endogenous to the species where said sample originates, and said bispecific antibody being non-covalently bound to a polymer probe, said probe comprising each of the following: a polymer backbone; a second antigen which is linked to said polymer backbone and which is recognizable by said second antibody; at least two detectable signal compounds linked to said polymer backbone.

2. A bispecific antibody complex according to claim 1 wherein said first and second antibodies are covalently linked in said bispecific antibody.

3. A bispecific antibody complex according to claim 1, wherein said polymer backbone is covalently linked to both said second antigen and said signal compounds.

4. The bispecific complex of claim 1 wherein said first and second antibodies each consist of one heavy and one light chain.

5. The bispecific complex of claim 1 further comprising a polymer probe being non-covalently bound to said bispecific antibody, said probe comprising each of the following: a polymer backbone; the non-endogenous second antigen which is linked to said polymer backbone and which is recognizable by said second antibody; at least two detectable signal compounds linked to said polymer backbone.

6. The bispecific complex of claim 4 further comprising a polymer probe being non-covalently bound to said bispecific antibody, said probe comprising each of the following: a polymer backbone; the non-endogenous second antigen which is linked to said polymer backbone and which is recognizable by said second antibody; at least two detectable signal compounds linked to said polymer backbone.

\* \* \* \* \*